United States Patent
Meldgaard et al.

(10) Patent No.: US 7,309,610 B2
(45) Date of Patent: Dec. 18, 2007

(54) ON-LINE MONITORING AND/OR CONTROL OF HEADSPACE IN A FLUID BED REACTOR SYSTEM

(75) Inventors: Morten Meldgaard, Holte (DK); Peer Herbsleb, Stovring (DK); Jacob Bjorholm, Copenhagen (DK); Ulf Houlberg, Lynge (DK)

(73) Assignee: Chr. Hansen A/S, Horsholm (DK)

( * ) Notice: Subject to any disclaimer, the term of this patent is extended or adjusted under 35 U.S.C. 154(b) by 545 days.

(21) Appl. No.: 10/311,477

(22) PCT Filed: Jun. 20, 2001

(86) PCT No.: PCT/DK01/00427

§ 371 (c)(1),
(2), (4) Date: Mar. 3, 2003

(87) PCT Pub. No.: WO01/97962

PCT Pub. Date: Dec. 27, 2001

(65) Prior Publication Data

US 2004/0107023 A1    Jun. 3, 2004

Related U.S. Application Data

(60) Provisional application No. 60/214,271, filed on Jun. 26, 2000.

(30) Foreign Application Priority Data

Jun. 22, 2000   (DK)   ................. 2000 00975

(51) Int. Cl.
    *G01N 30/02*   (2006.01)
(52) U.S. Cl. ....................................... 436/161
(58) Field of Classification Search .................. None
    See application file for complete search history.

(56) References Cited

U.S. PATENT DOCUMENTS 4,421,523 A    12/1983   Rogers et al.
4,684,456 A    8/1987    Van Driesen et al.

FOREIGN PATENT DOCUMENTS

EP    0 308 027 A    3/1989
FR    2 655 053 A    5/1991

OTHER PUBLICATIONS

J. Werther, "Messtechniken Fuer Gas/Feststoff-Wirbelschichtreaktoren", *Chemie. Ingenieur* Aug. 1, 1990, Technik,de,Verlag Chemie GmbH, Weinheim 62(8):605-612.

*Primary Examiner*—Yelena G. Gakh
(74) *Attorney, Agent, or Firm*—Foley & Lardner LLP

(57) ABSTRACT

The present invention relates to dynamically controlling the expansion of a fluid bed reactor system. By mounting a density detector to a floating body that floats on top of the carrying medium in the fluid bed, one can detect the density at a certain position that is level with the sensor head of the detector. Upon comparing the density detected with a predetermined density, the flow velocity of the carrying medium is adjusted accordingly.

12 Claims, 3 Drawing Sheets

Fig. 3

ON-LINE MONITORING AND/OR CONTROL OF HEADSPACE IN A FLUID BED REACTOR SYSTEM

FIELD OF INVENTION

The present invention relates in its broadest aspect to the field of detecting and/or controlling the dynamics e.g. the headspace, of a system comprising a spatially confined fluid bed of particles fluidised in a carrying medium. More specifically there is provided a novel method where transmitting means and receiving means are used for detecting a pre-determined particle density gradient formed within the fluid bed of fluidised particles whereby the dynamics of the system can be controlled.

TECHNICAL BACKGROUND AND PRIOR ART

A large number of target molecules i.e. compounds and other materials e.g. peptides, vitamins, hormones, lipids, proteins, enzymes, membranes, cells and the like and compounds from e.g. a petroleum or coal source can be reacted, separated and/or purified using chromatographic techniques. Such techniques include ion-exchange chromatography, reverse phase chromatography, hydrophobic interaction chromatography, affinity chromatography and mixed mode chromatography. For purification of a target molecule, the techniques are based on characteristics of the target molecule such as solubility, charge, size, shape or affinity, which cause the target molecule to be retained due to inter-actions/reactions with the chromatographic resin.

The affinity chromatography techniques make use of a specific binding between the target molecule and certain support particles or conglomerates e.g. as those described in WO 92/00799. Thus, a solution containing the target macromolecule to be purified is passed through a column containing an insoluble support (also termed a matrix material or a resin). The molecules that do not exhibit appreciable affinity for the matrix material will pass through the column, whereas those molecules that recognise the matrix material, and react with it, will be retained. The specifically adsorbed target molecule can then be eluted by any one of a number of procedures, which will effect dissociation by e.g. altering the composition or the pH of the carrying medium.

To improve effectiveness of affinity chromatography the use of fluid bed reactor systems (including fluidised and expanded bed systems) has been developed (Chase, H. A. and Draeger, N. M. 1992. Affinity purification of proteins using expanded beds. Journal of Chromatography 597:129-145). These fluid bed systems make it possible to apply liquids such as fermentation broths containing, in addition to the target molecule, whole cells, broken or ruptured cells or other materials with the potential of interfering with the binding of the target molecule to the chromatographic resins. In more conventional systems such other materials could cause problems manifested by an increase in the pressure drop across the fluid bed and the formation of a plug of trapped solids at the inlet of the bed. Accordingly, in such conventional systems it is most often necessary to apply a purification step before loading the material onto the chromatographic column. The fluidised or expanded bed systems have overcome these problems. In these systems the bed of particles is fluidised or expanded in an unconstrained configuration by a flow of fluid (up-flow or down-flow). When a critical minimum liquid or gas velocity is exceeded, the bed particles start to expand and gaps occur between the adsorbent particles which will allow particles other than the target molecule to pass freely through the bed. The fluid bed systems have been further improved by making support particles (matrix materials or resins) available which effect binding of specific target molecules and subsequently effect desorption or elution of the target molecules, thereby retaining the target molecules in the fluid bed and reducing the risk that the target molecules will pass through the system by the flow of the carrying medium.

In the fluid bed systems a headspace adjacent to the bed particles is most often needed in order to eliminate the risk that the bed particles will agglomerate at the top of the column as a consequence of the flow of the carrying medium. Therefore, most fluid bed systems are equipped with a membrane near the outlet adjacent to a volume substantially void of the bed particles, i.e. a headspace, which membrane is impermeable to the bed particles but permits the carrying medium to pass through the system. Such a headspace is most often needed in order to make the fluidised and expanded bed systems work. However, in most situations the size of the headspace volume must be kept at a minimum as the target molecules to be purified will be diluted by the presence of excess medium. Accordingly, it is of vital importance to detect and control the dynamics of the fluidised or expanded system in order to control the headspace volume and at the same time expand the matrix material to a degree that secures optimal purification of the target molecule.

Methods for detection and subsequent control of the particle expansion in fluid bed systems are known. Currently used control systems include the use of ultrasonic reflection from the interface between the carrying medium substantially void of particles (headspace) and the bed particles. This is, however, an unreliable method as gas bubbles and solid particles trapped in the headspace volume may disturb the signals. The presence of gas bubbles will cause the signal to disappear and solid particles in the headspace volume will give rise to noise signals.

In U.S. Pat. No. 4,684,456, a method for control of bed expansion is described. The method comprises the use of sources of radiation and radiation detectors, which are fixed pair-wise along the chromatographic column at a first, second and a third level. The detectors detect an attenuated signal whenever the bed surface is above the level of the detector and its corresponding radiation source. Hence, the position of the bed surface can be detected only as lying within one of the intervals defined by the levels. Accordingly, the expansion of the bed particles is only controlled by an on/off signal. Such a signal does not allow for a dynamic control of the expansion, as there will be no information on how far the bed surface is from any of the levels, and accordingly no possibility of adjusting the flow velocity to this situation.

In an SU Inventors Certificate No. 1696886 it is recognised that the interface between the particle bed and the headspace may be inhomogeneous and thus difficult and unreliable to use for control of the system dynamics. A method is described which detects the headspace, an "inhomogeneous phase boundary", in an expanded bed system. The method comprises providing a source of light and a sensor maintained at the same position in the fluid bed but not pointing towards each other. The sensor measures light from the source scattered by particles in the bed and thereby detects an average density coefficient of the fluidised particles. The method is based on performing repeated measurements under different flow conditions resulting in different volumes of the particle bed and consequently, different levels of the "inhomogeneous phase boundary"

between the bed particles and the headspace. Since different volumes of the particle bed are related to different average density coefficient, a relationship between the flow velocity and the measured average density coefficient of the fluidised particles can be obtained. This relationship can subsequently be correlated to the pre-established position of the "inhomogeneous phase boundary" in the system. This approach has to be repeated for each individual system that is to be controlled and a great amount of time has to be spent on calibrating the system before use.

In the EP patent application EP 308027 A, a method is disclosed for controlling the suspension density of a particulate solids and gas mixture from a vessel, to yield a uniform and constant mass flow to a reactor. The method comprises the use of sources of radiation and radiation detectors opposite, which are fixed pair-wise. The detector determines the suspension density, which is compared to a pre-selected value. It appears that EP 308027 A does not reveal a method for density gradient detection or for dynamic control of an expansion, which implies that no disclosure is given as to a dynamical adjustment of the flow according to a determined value of the density.

In a French patent application FR 655053 A, a method is provided for controlling the mass flow to a catalysed cracking process of carbohydrates. The method comprises the use of sources of ionised radiation and radiation detectors to measure the suspension density. The suspension density determined by the detector is compared to a pre-selected value. It is obvious that FR 655053 A does not describe neither density gradient detection nor dynamic control of an expansion. Hence, this patent application provides no method for dynamically adjusting the flow according to the determined density.

Accordingly, the prior art discloses unreliable or cumbersome ways of controlling the expansion of a fluid bed reactor system. It is well known that the flow velocity through the fluid bed system is the determinant of the other dynamics of the system including the volume of the headspace. Therefore, a control system is needed which, in a fast and reliable manner, detects the dynamics of a fluidised or expanded bed and controls the system by continuously adjusting the flow velocity of the carrying medium.

Such a control system could benefit from a transfer-function between a sensor activating signal and a sensor-output signal characterised as a continuous monotone function and the response time would be much faster and the system more accurate than known systems. Furthermore, such a sensor system will generate a much faster and more precise signal if the distance from the interface between the headspace medium and the mixture of medium and bed particles is based on measurements of a particular particle density gradient in the particle bed and thus, not simply relying on an on/off signal.

SUMMARY OF THE INVENTION

The present invention pertains to a method of detecting and/or dynamically controlling the expansion of a fluid bed reactor system comprising (i) a reactor vessel having an inlet and an outlet, the reactor vessel containing (a) a headspace volume of carrying medium substantially void of fluidised particles, and (b) a bed of fluidised particles in a carrying medium, the bed comprising a first volume where the particles are substantially homogeneously fluidised, and, between the first volume and the headspace volume, a second volume in which the fluidised particles form a particle density gradient, and, (ii) particle density detection means for detecting a pre-determined density of the fluidised particles at one or more positions in said second volume, said means being operationally connected to (iii) flow controlling means capable of being activated or deactivated by a signal from the density detection means generated by said detection means at the pre-determined particle density, the method comprising pre-setting the density of particles at said one or more positions in the second volume at which the density detection means generates a signal activating or deactivating the flow control means, whereby the expansion of a fluid bed reactor system is detected and/or dynamically controlled.

DETAILED DISCLOSURE OF THE INVENTION

The objective of the present invention is to provide a method of detecting and/or dynamically controlling the expansion of a fluid bed reactor system comprising a headspace volume of carrying medium substantially void of fluidised particles and, adjacent to that volume, a bed of fluidised particles in a carrying medium. As used in the present context the "expansion of a fluid bed reactor system" is to be understood as an expression covering the dynamics of the system including the expansion of the bed particles, the volume of the headspace, the flow velocity of the carrying medium and the composition of the medium.

Particularly, it is an objective of the present invention to provide a method which makes it possible to minimise the headspace volume of carrying medium substantially void of fluidised particles in the fluid bed reactor system by monitoring a particle density gradient formed within a second volume of the carrying medium comprising a bed of fluidised particles.

It is a new and inventive feature of the present invention that it makes use of a recently found feature of fluid bed systems, that the fluid bed comprises a particle density gradient under all flow conditions, which provides a useful basis for dynamically detecting and/or controlling the dynamics of the system.

It has been found that the particle density gradient formed within the fluidised or expanded bed of particles can be used for detection and/or control of the dynamics of the system by any suitable control system. Such control systems may include an electromagnetic transmitter and receiver as described below. The transmitter and the receiver may be positioned in the mixture of carrying medium and particles where the fluid bed forms a particle density gradient. Thereby, the receiver will receive a signal depending on the mixture of carrying medium and bed particles in the fluid bed. Alternatively, either one, or both, of the transmitter and the receiver may be positioned outside the volume where the fluid bed forms a particle density gradient. However, at a position so that at least part of the radiation from the transmitter received by the receiver traverses the volume where the fluid bed forms a particle density gradient. The signal from the transmitter and the receiver can subsequently be transferred to a regulator whereby the dynamics of the system can be controlled.

Thus, the present invention provides an advantageous method for controlling the dynamics of a fluid bed reactor system, such as an expanded bed or a fluidised bed, using this particle density gradient for detection and control. The present invention utilises the variation of the density of particles throughout the fluid bed. Thus, the invention allows control of the dynamics of the fluid bed at any desired or pre-determined density of the bed particles, at any position within the particle density gradient of the fluid bed. It is possible to control the system according to the invention by one particle density gradient, however, two or more particle density gradients may also be used for a dynamic control of the flow controlling means. Hereby, the flow controlling means can be activated or deactivated by a signal from the density detecting means based on a difference between a first and a second particle density gradient at any position in the second volume of the bed. It is contemplated that any number of particle density gradients and thus, any number of densities detecting means may be used for detection and control of the expansion of the fluid bed system.

As used in the present context, the term "density" is used in its broadest sense to describe the degree to which a volume or area is filled with particles. The density may refer to a total density of all particle species in the medium or to partial density of a specific species only. The density is typically measured in numbers per unit volume or numbers per unit area, or where appropriate, quantity of material per unit volume or per unit area. This means that at least the carrying medium and the bed particles are determinants for the particle density gradient of the system. However, any added element or material may also contribute to the total density detected, and optionally be used for control of the fluid bed system dynamics. As used in the present context the term "density" also covers the contribution of the macrostructure of the bed particles, and particles applied to the system through the carrying medium, e.g. the surface structure, to the total density of the system.

Additionally, the term "density of mass" will be used to denote the density in grams/cm$^3$, or equivalent, for any substance or mixture in the system. Hence, the density of mass is used when considering whether one substance will float or sink in relation to another substance.

The fluid bed reactor system of the present invention comprises a reactor vessel having an inlet and an outlet, the reactor vessel containing a headspace volume of carrying medium substantially void of fluidised particles, and a bed of fluidised particles in a carrying medium. The phase between the headspace volume and the volume of fluidised particles is characterised as an "interface". It will be appreciated by the person of skill in the art that the "interface" will not necessarily constitute a sharp demarcation between the headspace volume and the volume of carrying medium comprising fluidised particles.

The fluid bed reactor system of the present invention includes expanded bed systems and fluidised bed systems and any combinations hereof. These systems include up-flow fluid reactor systems having a fluid inlet at the bottom of the reactor vessel and fluid bed particles of a specific density of mass larger than that of the carrying medium. However, down-flow fluid bed reactor systems having a fluid inlet at the top of the reactor vessel and fluid bed particles of a density of mass less than the carrying medium is also encompassed. In the down-flow systems a headspace is formed near the bottom of the fluid bed reactor vessel.

The up-flow system may be equipped with a device, which can control the volume of the reactor system. Such controlling devices may include a floating body equipped with an outlet. A floating body is preferably made of a material, which permits it to float on top of the headspace volume. The advantage of such a floating outlet is the possibility to reduce the headspace volume of the system by allowing the adjustment of the headspace in relation to expansion of the bed particles. Hence, the floating outlet allows for a more flexible reactor system. In the fluid systems large quantities of liquid is used. Reducing the headspace volume leads to a more pure and concentrated and thus, a more valuable product.

The particle density gradient is formed in the second volume of the bed of fluidised particles between a first volume of substantially homogeneously fluidised particles and the headspace volume. The volume of the fluid bed of particles in the carrying medium comprises a first volume where the particles are substantially homogeneously fluidised and, a second volume where the fluidised particles form a particle density gradient. The ratio between the first and the second volume is typically in the range of 1:99-99:1 such as in the range of 5:95-95:5, including the range of 10:90-90:10 such as the range of 15:85-85:15 including the range of 25:75-75:25. The particle density gradient can be detected by any suitable means therefor including particle density detecting means as defined below.

The particle density gradient as defined above is formed in a fluid bed system contained in a reactor vessel. In the present context such a "reactor vessel" is to be understood as any suitable confinement comprising bed particles such as a chromatographic column. The confinements may include a vertical reactor vessel with an inlet, an outlet, a fluid bed of particles, a carrying medium and most often a headspace volume substantially void of bed particles. The carrying medium is introduced at the inlet and dispersed, optionally through a gas head in case of down-flow reactor systems, through the bed of particles, which are suspended and fluidised in the medium. The carrying medium is conducted through the fluid bed reactor system and a pool of reacted and/or unreacted fluid is let out at the outlet. If desired, the reactor vessel is provided with means for obtaining even distribution of flow. At zero flow or after a period with zero flow the bed particles will be referred to as "settled", in this situation it may still be possible to detect a particle density gradient in the settled bed of particles.

As used in the present context the term "activating or deactivating flow" refers to a dynamic control of the flow controlling means. By "activating" is meant the situation where the flow velocity is increased at any level relative to the existing flow and by "deactivating" is meant the situation where the flow velocity is decreased to any level relative to the existing flow.

The fluid bed reactor system of the invention may advantageously be used in chromatographic systems using non-packed columns and the chromatographic systems may be selected from the group consisting of liquid chromatography, ion-exchange chromatography, biospecific affinity chromatography such as immunosorption and protein A chromatography, and a group specific affinity chromatography such as hydrophobic, thiophilic, dye, lectin, and metal chelate chromatography. The system may further be used in: filtration of a fluid medium, adsorption of at least one selected substance present in a fluid medium, heterogeneous catalysis of a reaction taking place in a fluid medium, immuno-chemical procedures, including immunosorption, solid-phase synthesis and solid-phase oligonucleotide synthesis, microbial procedures, enzyme reactor procedures, carriage on the outer or the interior surface of the fluid bed particles, optionally after a suitable surface treatment, of live cells selected from cells of human, animal, plant, fungal or micro-organism origin.

Accordingly, in one suitable embodiment the system of the present invention is used for the separation of proteins from a carrying medium such as a fermentation broth.

The bed particles of the fluid bed system may be reactive or may carry immobilised reactive components such as ligands selected for a fluid phase of chemical or physical processes as defined herein below. Further, the fluid bed particles may comprise any material suitable for a specific physical, mechanical, chemical or biological process and may include conglomerating agents and active substances as described in WO 92/00799, which is hereby incorporated by reference. Such conglomerating agents are defined as a composite of basic particles, which may comprise particles of different types and sizes, held together by conglomerating agents. Such conglomerates may be of various size and shapes and should preferably exhibit various degrees of mechanical rigidity depending on the application. Further, the conglomerates may be chemically active or may be chemically inactive under the conditions applied.

The particles for use in the system of the present invention include particles of high and low density of mass as described hereinbefore and they may be chosen in order to provide a certain relative density of mass with respect to the carrying medium of the system. Thus, particles can be chosen with respect to the density of mass of the carrying medium for their particular purpose of application, including proper consideration of the influence of their sizes and structure on their floating or sedimentation properties.

The particles for use in the present invention may include particles of any suitable material selected from the group consisting of: natural and synthetic organic and inorganic monomers and/or polymers such as natural and synthetic polysaccharides and other carbohydrate based polymers, including agar, alginate, carrageenan, guar gum, gum arabic, gum ghatti, gum tragacanth, karaya gum, locust bean gum, xanthan gum, agarose, cellulose, pectins, mucins, dextrans, starches, heparins, gelatins, chitosans, hydroxy starches, hydroxypropyl starches, carboxymethyl starches, hydroxyethyl cellulose, hydroxypropyl cellulose, and carboxymethyl celluloses and any mixtures of these. The particle materials may also be selected from the group consisting of: synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such organic polymer functionality, and substituted derivatives thereof and any mixtures of these.

The size of the bed particles may be in the range of 1-10000 μm such as in the range of 1-5000 μm, including the range of 1-4000 μm, 1-3000 μm, 1-2000 μm, 1-1000 and in the range of 10-10000 μm such as in the range of 50-5000 μm including the range of 50-2500 μm, 50-1000 μm, 50-750 μm, 50-500 μm and 100-500 μm.

The bed particles used in the method of the present invention are preferably fluidised by applying a flux of a carrying medium to the fluid bed. Such a carrying medium may be any material that can be introduced into the system of the invention and includes liquids, gasses and particles optionally carrying target molecules. The carrying medium also includes the medium used for eluting the target molecules from the matrix material of the system.

Generally, fluid bed systems such as fluidised and expanded bed systems are operated under flow conditions resulting in an even and smooth distribution of fluidised particles in the fluid bed and substantially without turbulence in the fluid bed of particles. It is however contemplated that a more turbulent flow may be applied to the system still forming a particle density gradient, which can be used for detection and control. It is contemplated that the flow applied to the fluid bed reactor system is often a mixture of a laminar flow and a turbulent flow.

The flow of the carrying medium through the fluid bed system is characterised as an up-ward or alternatively, a down-ward flux of the medium through a horizontal cross section of the reactor system Such fluxes are typically applied at rates of 0,1-100 ml $cm^{-2}$ $min^{-1}$ However, 2-20 ml $cm^{-2}$ $min^{-1}$ is often preferred and it may even be advantageous to use a flow rate of about 3-12 ml $cm^{-2}$ $min^{-1}$ These rates depend on the type of matrix used. The heavier the matrix the greater rate of the carrying medium without too large expansion. By "too large" is meant that the matrix flows out of the column.

It is an essential feature of the method according to the present invention that particle density detection means are provided for detecting a pre-determined density of the fluidised particles at one or more positions in the second volume of the fluidised bed. In the present context, "means for detecting the density of fluidised particles in the fluid bed" typically comprises a transmitter for transmitting a signal, which traverses at least part of the fluid bed volume forming a particle density gradient, and a receiver for receiving at least part of the transmitted signal. The detection of the density of fluidised particles typically depends on an alteration of the transmitted signal due to the fluidised particles or other solid material as defined earlier. The alteration may be caused by absorption and/or scattering of parts of the signal by the bed particles, such absorption of parts of the signal propagating in specific directions or, if the signal is an alternated signal, by absorption and/or scattering by the bed particles of one or more specific frequencies of the spectrum of the signal. Alternatively, the particle density may be determined by the fluorescence or phosphorescence from particles illuminated by the transmitter if the transmitter comprises a source of electromagnetic radiation such as a laser. Hence, the detection of the particle density gradient relates to the difference between the transmitted signal and the received signal, such as parts of the transmitted signal lacking in the signal received by the receiver. Typically, these alterations, taking place in the presence of the bed particles, will attenuate the received signal in relation to the transmitted signal. In one embodiment of the present invention, the detecting means may even be capable of detecting a particle density gradient in the settled bed of particles.

The transmitter preferably transmits an electromagnetic radiation signal. Alternatively, the transmitter may transmit a signal such as an audio signal, electric or paramagnetic signal or radioactive radiation. The transmitter may be an electromagnetic radiation source such as a laser including an LED (light emitting diode). The signal may include electromagnetic signals selected from the group consisting of at least substantially monochromatic signals, signals comprising radiation with a plurality of frequencies, typically a continuous range of frequencies within a given interval, coherent radiation signals and incoherent radiation signals. Alternatively, the transmitter may be an electric circuit adapted to generate an electric or magnetic signal, a speaker or other means for generating pressure waves, and a radioactive source. It is contemplated that mechanical signals may be applied to the system in order to detect the particle density gradient. Such mechanical devices may include a floating body of specific density of mass in the fluid bed of particles, which may be used to signal the position of the pre-determined particle density gradient.

The receiver is preferably adapted to receive the signals from the transmitter and will hence preferably be means for sensing or detecting electromagnetic radiation such as a photodiode, an antenna or other signal conditioning devises. In the alternatives mentioned above, the receiver may be receiving means for sensing or detecting an electric or magnetic signal, a microphone or other means for sensing or detecting pressure waves, and a radioactivity detector.

The transmitter and the receiver may comprise a number of individual transmitters/receivers, and may be positioned in contact with the bed or physically separated from the bed, such as outside the reactor system. In a preferred embodiment of the method of the present invention the particle density detecting means are positioned on a floating body on top of a headspace volume and capable of detecting the density gradient of the fluidised particles. Moreover, the signals may be generated and detected elsewhere and guided to/from the spatial confinements of the bed trough guiding means such as a wave guide including an optical fibre.

The detecting means preferably further comprises a controller for controlling the operation of the transmitter and the receiver. Also, the transmitter and the receiver are preferably operationally connected to a processor for processing the output of the receiver in order to generate an output from the received modulated signal, the output being correlated to the density of the bed traversed by the transmitted signal. The detecting means are operationally connected to flow controlling means whereby the flow of the carrying medium can be activated or deactivated, optionally by a control loop, whereby in turn the dynamics of the reactor system can be controlled.

DESCRIPTION OF DRAWINGS

The invention is further illustrated in the following non-limiting examples and in the figures, where.

EXAMPLE 1

Figure 1:
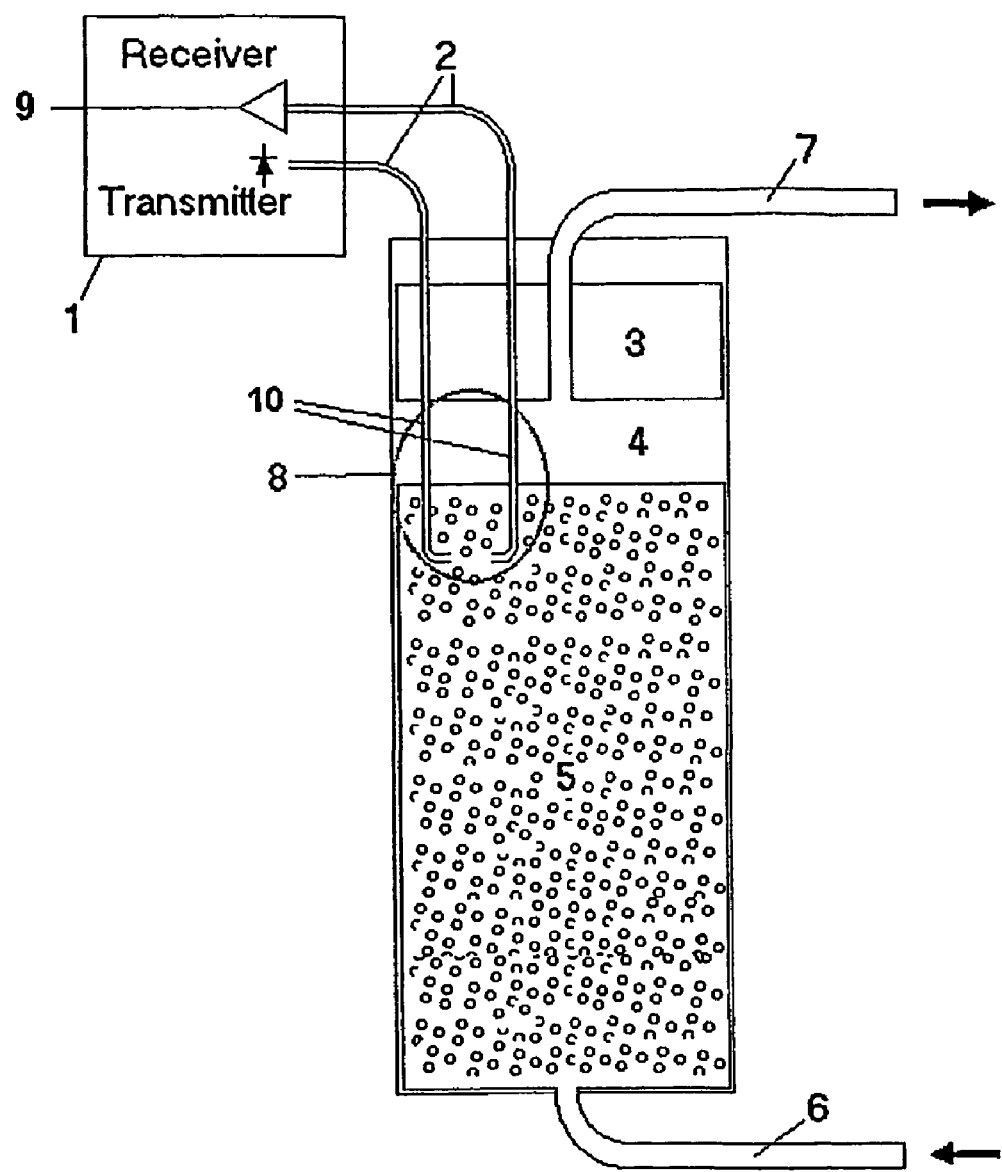
FIG. 1 is a schematic diagram of a fluid bed reactor system set-up illustrating the important components of the reactor system of the invention.

The fluid bed reactor system is illustrated in FIG. 1 and consists of a cylindrical column in which the particles suspended in the carrying medium are contained. The medium 6 is pumped into the bottom of the column whereby the volume of the particles suspended in the medium is expanded. The medium is pumped out of the column through an outlet 7 mounted on a floating body 3. Hereby, two volumes are formed in the column: One fluid bed phase 5 containing particles suspended in the medium and one phase 4 substantially void of particles but containing media (headspace).

EXAMPLE 2

Monitoring of the interface between the headspace and the fluid bed of particles suspended in the medium does not allow for dynamic control of the fluid bed system, as the signal would be an on/off signal indicating whether the interface was above or below the level of detection. However, it was found that an electromagnetic radiation signal traversing the fluid bed was not totally extinguished but actually showed a significant signal. Furthermore, it was found that this signal was dependent on the position of the sensor in respect to the interface between the headspace and the fluid bed of particles suspended in the medium. Thus, it was possible to detect particle density gradients within the fluid bed of particles, which could be used as a tool in controlling of the expansion of the system. It was expected that the macrostructure of the particles e.g. size, shape, material etc. and material in the carrying medium would effect the signal. Therefore a transmitting signal at frequencies in the range between 500-1100 nm was tested in order to optimise the sensor system.

An exemplary sensor system of the present invention is illustrated in FIG. 1 and comprised the following parts:

1. Sensor head 8
2. Fiber optical cable 2
3. Optical Transmitter and receiver 1
4. Analogue signal output 9

The sensor head 8 is formed of two stainless steel tubes 10, bent in such a way that the two ends face each other at a distance of about 20 mm. In each stainless steel tube, in tight connection with the inner wall of the tube, an optical fiber 2 is mounted. The aperture of the optical fiber is about 1 mm. As a result of the distance between the ends, the structure of the media and the nature of the light, the received light was a mixture of scattered and direct actuated light.

Figure 2:
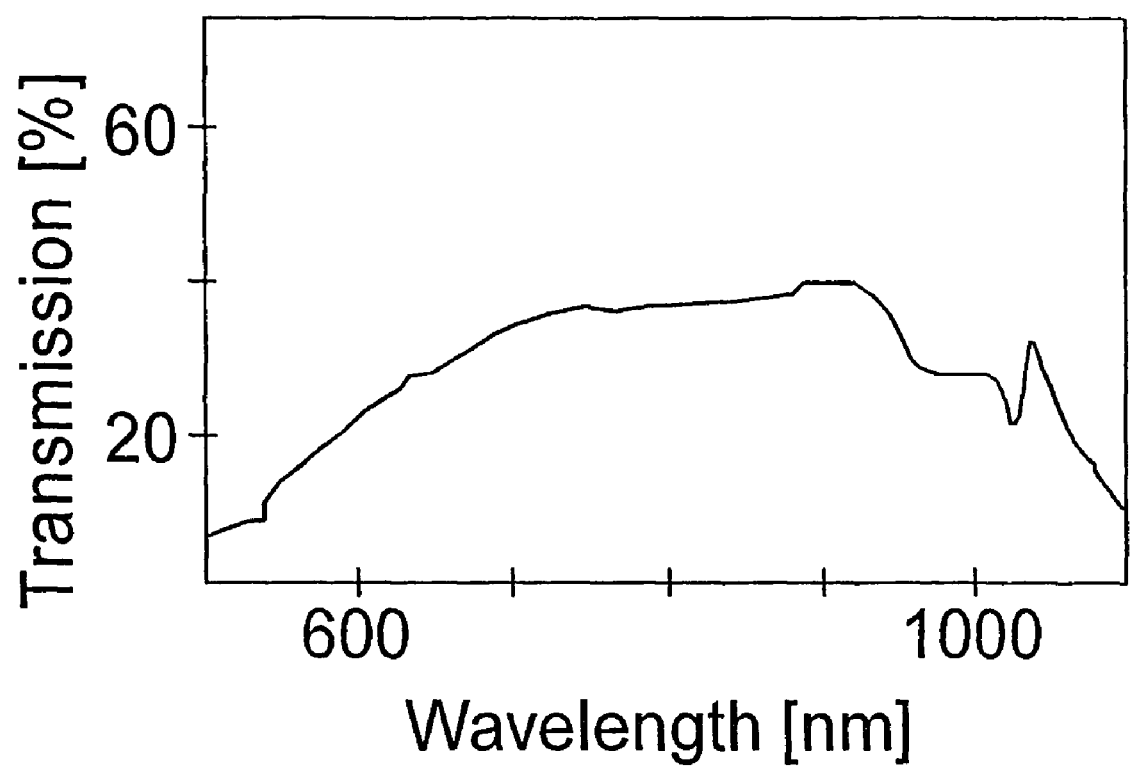
FIG. 2 is a graph showing the transmission of light at different wavelength. A wavelength of 660 nm was used for subsequent studies in the reactor system of the invention; and, FIG. 3 is a graph showing the particle density gradient in the first 12 cm of the fluid bed of particles below the headspace volume.

A specific mixture of particles (agarose with glass beads incorporated) in a 25 mM $PO_{4-}$ buffer, pH 5.5 was placed in a spectrophotometer. The wavelength of the transmitter was varied and FIG. 2 shows a frequency spectrum of the received electromagnetic radiation. The Figure clearly illustrates that a transmitting signal between 600 and 1000 nm resulted in the most significant signal, as a plateau in the spectrum was obtained between these frequencies. A transmitting signal of 660 nm was chosen in the sensor system used in the following examples.

EXAMPLE 3

The sensor system as described and operated in Example 2 was used to verify the existence of a particle density gradient in a fluid bed of particles. The optical transmitter 1 produced a monochromatic and incoherent and pulse modulated beam of light at a frequency of 660 nm. The receiver 1 demodulated the signal and formed an analogue signal 9 corresponding to the received signal. The transmitter and receiver were physically contained in the same unit.

The analogue output signal 9 from the receiver was proportionate to the power of the received signal relative to the power of the transmitted signal. Alternatively, the intensity, luminosity or fluence of the received signal can be measured, depending on the specific set-up. The mixture of fluid bed particles and the carrying medium causes the difference in transmitted and received signal.

Figure 3:
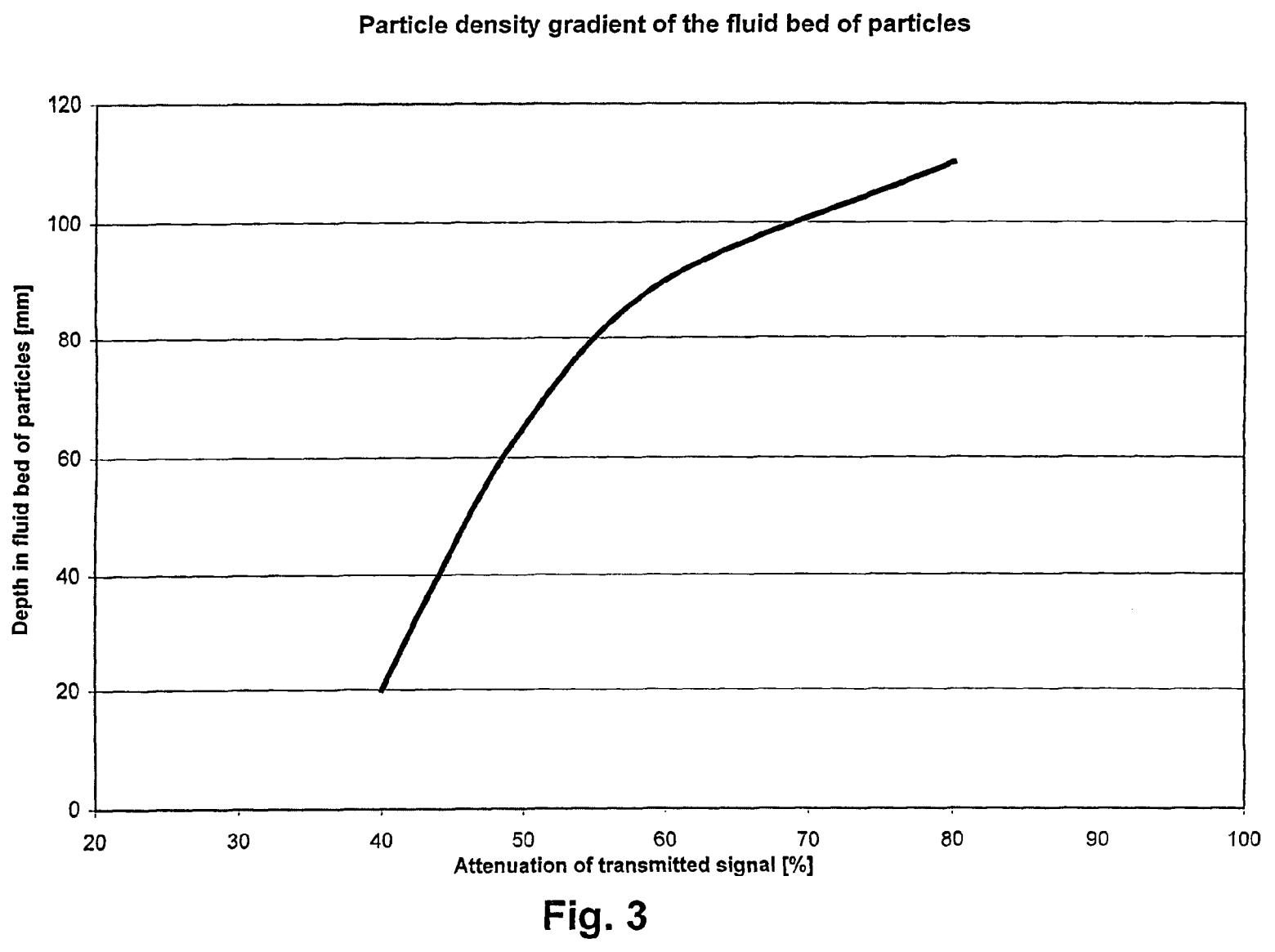

The sensor head 8 was mounted on the floating body 3 so that the ends of the stainless tubes 10 were at a given distance below the surface of the carrying medium. Subsequently, the headspace was adjusted whereby the sensor head was positioned at different levels below the interface between the headspace and the fluid bed of particles. The result is illustrated in FIG. 3 showing the attenuation of the transmitted signal when the sensor head was positioned at different distances from the interface between the headspace and the fluid bed of fluidised particles. As the figure clearly illustrates, a particle density gradient was formed within the fluid bed.

As described above, the particle density gradient formed in the fluid bed reactor system depends on the particle composition and the carrying medium applied to the column.

Hereby, a pre-determined level of all particles contributing to the particle density gradient of the system can be obtained and subsequently used for a detection and control of the system.

EXAMPLE 4

In this example the dynamics of the system being detected and controlled were the headspace volume 4 of the system. The particle density gradient as illustrated in FIG. 3 was used for establishing a pre-determined particle density corresponding to a predetermined attenuation of the signal, which was used for detection and control of the headspace volume 4.

The sensor head was mounted in the floating body 3 so that the ends of the stainless tubes 10 were at a given distance below the surface of the carrying medium. The attenuation of the signal depends on the distance from the interface between the headspace 4 and the fluid bed of particles 5 to the position of the ends of the stainless steel tubes 10 in the fluid bed of particles 5.

Since the attenuation was held on a predetermined value corresponding to a predetermined depth in the fluid bed according to FIG. 3, and since the ends of the stainless steel tubes 10 were fixed at a specific distance from the floating body, the signal corresponded to a given height of the headspace. Accordingly, the analogue output signal 9 was used for monitoring and controlling the headspace. The signal 9 was used for controlling the headspace as the output of the regulator was operationally connected to a pump that removed carrying media from the headspace.

EXAMPLE 5

In this example the dynamics controlled were the expansion of the volume of the fluid bed of particles 5. The particle density gradient as illustrated in FIG. 3 was used for establishing a pre-determined particle density corresponding to a predetermined attenuation of the signal, which were used for detection and control of the volume of the fluid bed of particles 5.

The sensor head was mounted at a fixed position in the column, and since the signal was dependent on the distance from the interface between the headspace 4 and the fluid bed of particles 5 to the position of the ends of the stainless steel tubes 10, the signal corresponded to a given position of the surface of the mixture of particles in the column. Thus, the predetermined signal corresponded to the expansion of the volume of the fluid bed of particles 5. The analogue output signal 9 was used for control of the expansion as the output signal of the regulator was used to control the pump that feed media into the column.

EXAMPLE 6

The penetrability of electromagnetic radiation at a certain frequency varies with respect to the mixture of bed particles and particles in the carrying media. Thus, by detecting the attenuation at specific frequencies, it was possible to detect the mixture of particles.

The sensor head was mounted at a fixed position relative to the expansion of the fluid bed of particles 5. In this position the signal varied in respect of the mixture of particles. Thus, it was possible to detect a specific particle composition between the fluidised particles of the bed and particles applied to the column.

The invention claimed is:

1. A method for dynamically controlling the expansion of a fluid bed reactor system, comprising:
   (i) providing a reactor vessel that has an inlet and an outlet and that contains:
      (a) a headspace that comprises carrying medium and that is substantially void of fluidized particles, wherein said carrying medium is a liquid,
      (b) a bed of fluidized particles in the carrying medium, and
      (c) a floating body that floats on top of the carrying medium in said headspace;
   (ii) providing at least one particle density detector comprising an electromagnetic transmitter, a receiver and a sensor head, wherein:
      (a) said density detector is mounted to said floating body such that the sensor head is positioned in said bed of fluidized particles,
      (b) said density detector detects the density of the fluidized particles in said bed of fluidized particles at a position that is level with said sensor head, and
      (c) said density detector generates a signal upon comparing the density detected with a pre-determined density;
   (iii) providing a flow controller that controls the flow velocity of the carrying medium according to the signal from said density detector;
   (iv) measuring and comparing continuously the density of the fluidized particles with the pre-determined density by said first density detector; and
   (v) continuously adjusting the flow velocity of said carrying medium by said flow controller as a function of said measuring and comparing.

2. A method according to claim 1 wherein the reactor vessel is a chromatographic column.

3. A method according to claim 1, wherein the fluidized particles are of a size in the range of 1-10000 μm.

4. A method according to claim 1, wherein the fluidized particles comprise a material selected from the group consisting of natural and synthetic organic polymers, inorganic substances, and any mixtures hereof.

5. A method according to claim 1 wherein the carrying medium is a fermentation broth.

6. A method according to claim 1, wherein the flow of the carrying medium is selected from the group consisting of a laminar flow and a turbulent flow.

7. A method according to claim 1, wherein the flow rate of the carrying medium is within the interval of 0.1-100 ml $cm^{-2}$ $min^{-}$ cross sectional area of the confined space, such as 2-20 ml $cm^{-2}$ $min^{-1}$ and 3-12 ml $cm^{-2}$ $min^{-1}$.

8. A method according to claim 1, wherein the fluidized particles form a settled bed.

9. A method according to claim 1, wherein the measuring of step (iv) comprises:
   (a) measuring the attenuation of the transmitted signal by comparing the received signal with the transmitted signal; and
   (b) determining the density of the fluidized particles by correlating with the attenuation.

10. A method according to claim 1, wherein said density detector is operationally connected to said flow controller by a control loop.

11. A method according to claim 1, wherein said transmitter and said receiver are operationally connected to a processor that processes the output of said receiver.

12. A method according to claim 1, wherein the flow of the carrying medium is a mixture of a laminar flow and a turbulent flow.

* * * * *